(12) United States Patent
Zagzebski et al.

(10) Patent No.: US 7,601,122 B2
(45) Date of Patent: Oct. 13, 2009

(54) ULTRASONIC ELASTOGRAPHY WITH ANGULAR COMPOUNDING

(75) Inventors: James A. Zagzebski, Madison, WI (US); Tomy Varghese, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 700 days.

(21) Appl. No.: 10/765,293

(22) Filed: Jan. 27, 2004

(65) Prior Publication Data

US 2004/0215075 A1 Oct. 28, 2004

Related U.S. Application Data

(60) Provisional application No. 60/464,678, filed on Apr. 22, 2003.

(51) Int. Cl.
*A61B 8/00* (2006.01)

(52) U.S. Cl. .................. 600/449; 600/443; 600/561; 600/587; 600/438; 600/459

(58) Field of Classification Search .......... 600/443, 600/449, 561, 587, 438, 459; 73/584
See application file for complete search history.

(56) References Cited

U.S. PATENT DOCUMENTS

| | | | | |
|---|---|---|---|---|
| 4,649,927 A | | 3/1987 | Fehr et al. | |
| 5,524,636 A | * | 6/1996 | Sarvazyan et al. | 600/587 |
| 6,068,597 A | * | 5/2000 | Lin | 600/443 |
| 6,270,459 B1 | | 8/2001 | Konofagou et al. | |
| 6,377,656 B1 | * | 4/2002 | Ueki et al. | 378/98.7 |
| 6,984,209 B2 | * | 1/2006 | Hynynen et al. | 600/438 |
| 2003/0171672 A1 | | 9/2003 | Varghese et al. | |
| 2004/0254460 A1 | * | 12/2004 | Burcher et al. | 600/437 |

OTHER PUBLICATIONS

Ophir J. et al., Elastographic Imaging, Ultrasound in Medicine and Biology, New York, NY, vol. 26, May 2000, pp. S23-S29.
O'Donnell M. et al., Optimum Displacement for Compound Image Generation in Medical Ultrasound, IEEE Transactions on Ultrasonics, Ferroelectrics and Frequency Control, IEEE Inc., New York, vol. 35, No. 4, Jul. 1988, pp. 470-476.
Burckhardt, C.B., Speckle in Ultrasound B-mode Scans. IEEE Transactions on Sonics and Ultrasonics 1978; 25: 1-6.

\* cited by examiner

*Primary Examiner*—Brian Casler
*Assistant Examiner*—Nasir Shahrestani
(74) *Attorney, Agent, or Firm*—Boyle Fredrickson, S.C.

(57) ABSTRACT

Ultrasonic strain measurements, which characterize the structure of tissue, may be obtained by combining multiple echo signals acquired at different compressions and at different angles. Such angular compounding may improve the quality of the elastic signal and provide at one time both an axial and lateral strain measurement.

41 Claims, 6 Drawing Sheets

ULTRASONIC ELASTOGRAPHY WITH ANGULAR COMPOUNDING

CROSS-REFERENCE TO RELATED APPLICATIONS

This application claims the benefit of U.S. Provisional Application 60/464,678 filed Apr. 22, 2003 hereby incorporated by reference.

STATEMENT REGARDING FEDERALLY SPONSORED RESEARCH OR DEVELOPMENT

This invention was made with United States government support awarded by the following agencies:
NIH CA 39224.
The United States has certain rights in this invention.

BACKGROUND OF THE INVENTION

The present invention relates to ultrasonic medical imaging and in particular to an improved apparatus and method for making ultrasonic elastography images.

Elastography is a new imaging modality that reveals the stiffness properties of tissue, for example, axial strain, lateral strain, Poisson's Ratio, Young's Modulus, and other common strain and strain-related measurements. The strain measurements may be collected over an area and compiled as a two-dimensional array of data, which may then be mapped to a gray or color scale to form a strain "image". Analogously, strain measurements may be collected over a volume displayed either three-dimensionally or as a series of stacked two-dimensional images.

In quasi-static elastography, two images of the tissue may be obtained by the ultrasound device in two different states of compression, for example, no compression and a given positive compression. The tissue may be compressed by an external agency such as a probe or the like, or may be compressed by muscular action or the movement of adjacent organs. Strain may be deduced from these two images by computing gradients of the relative local shifts or displacements in the images along the compression axis. Quasi-static elastography is analogous to a physician's palpation of tissue in which the physician determines stiffness by pressing the tissue and detecting the amount the tissue yields under this pressure.

In dynamic elastography, a low-frequency vibration is applied to the tissue and the tissue vibrations are measured, for example, using Doppler detection.

Ultrasonic elastographic images may have considerable image noise arising from a number of sources. In quasi-static elastography, one noise source is so-called "correlation artifacts" which relate to the amount of overlap in the windows of correlation as may be reduced improve resolution.

A number of techniques have been used to minimize these image artifacts, including: global temporal stretching in which the post-compression echo signal is stretched by a known compression factor before estimating axial strain, wavelet de-noising where wavelet techniques are used to smooth the displacement estimates in the wavelet domain without losing edge information, and multi-compression averaging in which multiple readings are taken with smaller compression increments and averaged together.

Typically elastography produces a strain measurement only along the axis of compression. However, lateral strain may be of value both in deducing qualities like Poisson's Ratio and in countering the effects of lateral motion in de-correlating the axial displacement of the tissue. In addition, shear strain images can also be obtained.

Two principal methods have been used to obtain lateral strain. The first described in U.S. Pat. No. 6,270,459 interpolates between successive axial rays or echo signals to provide a basis for horizontal displacement measurement using a correlation technique. A second technique makes the assumption that the tissue being measured is incompressible and simply deduces lateral strain from the axial strain.

SUMMARY OF THE INVENTION

The present invention provides a method and apparatus to significantly decrease image artifacts in elastographic imaging by using multiple angle acquisitions combined either before or after strain is extracted. The inventors have determined that even a relatively small angular difference between acquisitions provides the necessary statistical independence of the measurements to significantly reduce image noise. This angular compounding concomitantly provides both axial and lateral strain measurements.

Specifically, the present invention provides an ultrasonic elastography system including an ultrasonic transducer system adapted to provide a set of echo signals from at least two angles from a plurality of voxels in a region of interest. The set of echo signals includes first echo signals taken with the region of interest in a first compressive state (e.g. no compression) and a second echo signal taken with the tissue of the region of interest in a second compressive state. A processor combines at least portions of the set of echo signals from different angles to produce at least one compounded strain measurement for voxel in the region of interest.

Thus is it one object of the invention to provide a simple method of decreasing the statistical fluctuation in elastographic measurements to improve image quality and quantitative accuracy.

The processor may use the angle of the ultrasonic echo signal underlying the strain measurement to convert the strain measurement to an equivalent strain measurement along a predetermined strain axis and may combine the converted strain measurements to produce the compounded strain measurement.

Thus is it another object of the invention to provide a method of combining strain measurements made at different angles to improve strain measurements made along a given angle by converting the multiple strain measurements to a common strain axis before combination.

The predetermined strain axis may be the axis of compression or may be an axis lateral to that axis.

Thus it is another object of the invention to provide strain measurements along arbitrary axes.

The angle of compression of the tissue may remain constant for the different angles of echo signal. Alternatively, the angle of compression may change with changes in the angle of the echo signal.

Thus it is another object of the invention to flexibly provide for single or multi-angle compressions to be used in extracting additional information from the tissue.

These particular objects and advantages may apply to only some embodiments falling within the claims and thus do not define the scope of the invention.

DETAILED DESCRIPTION OF THE PREFERRED EMBODIMENT

Figure 1:
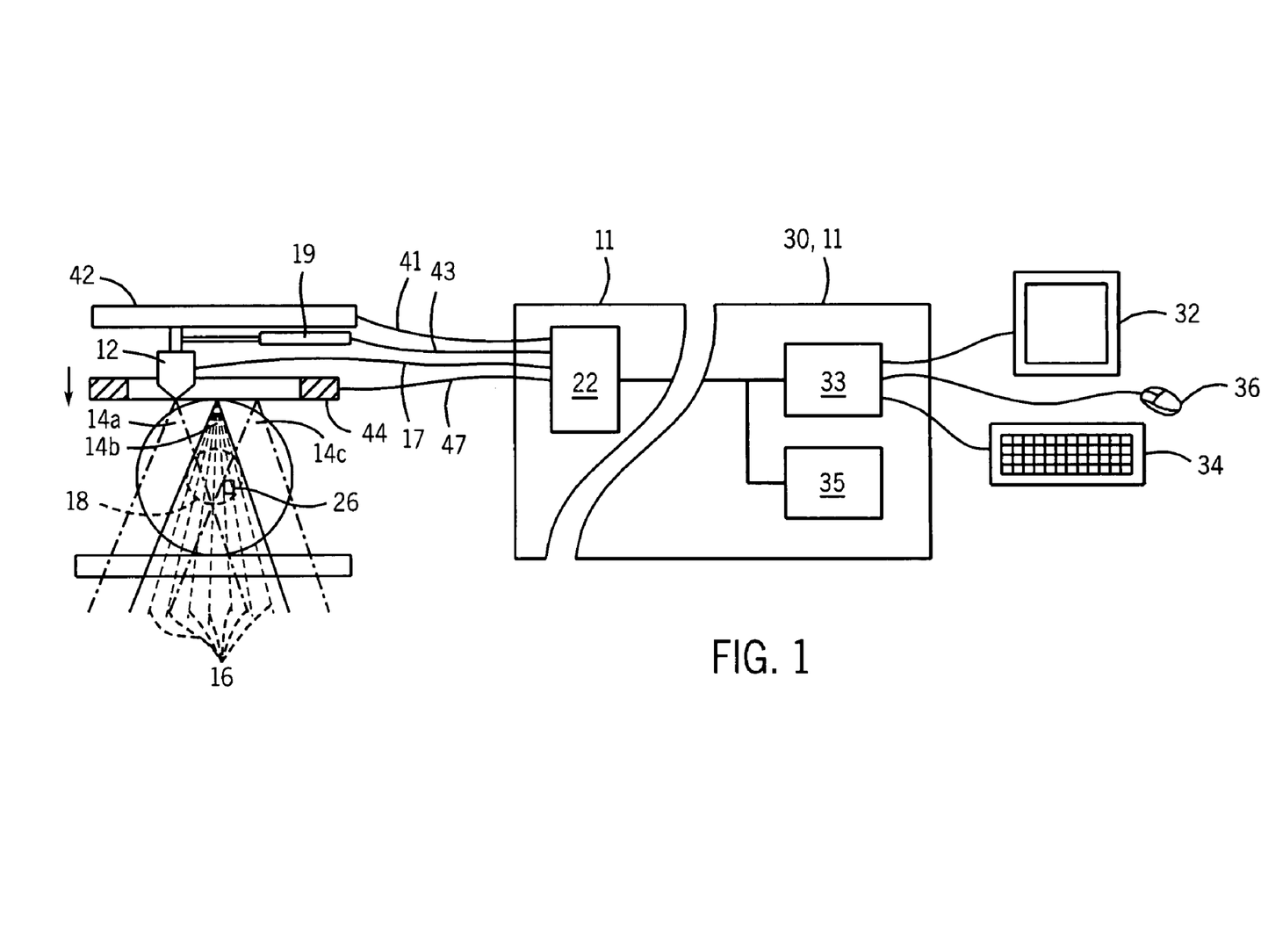
FIG. 1 is a simplified block diagram of an ultrasound scanner suitable for use with the present invention.

Referring now to FIG. 1, an elastographic imaging system 10 suitable for use with the present invention may employ an ultrasonic imaging machine 11 alone or in combination with an external computer 30. Generally, the ultrasonic imaging machine 11 provides the necessary hardware and/or software to collect the series of ultrasonic echo signals that can be further processed as will be described by a processor 33 held within the ultrasonic imaging machine 11 in the external computer 30.

An ultrasonic transducer 12, associated with ultrasonic imaging machine 11, may transmit multiple ultrasonic beams 14a, 14b, and 14c (only three shown for clarity) toward a region of interest 18 within a patient. Ultrasonic beam 14b, which typifies the ultrasonic beams 14, produces echoes along different measurement rays 16 acquired at different angles within each ultrasonic beam 14. Different rays 16 will pass through different volume elements (voxels) 26 within the region of interest 18 and generally a given voxel 26 will have multiple rays 16 passing through it at different angles from different ultrasonic beams 14.

The echoes along each of the rays 16 will be received by the transducer 12 and converted to electrical echo signals 17 acquired through the interface circuitry 22 of the ultrasonic imaging machine 11. The interface circuitry 22 may provide amplification, digitization, and other signal processing of the echo signals 17 as is understood in the art. These digitized echo signals may then be transmitted to a memory 35 for storage in subsequent processing by processor 33 as will be described.

Ultimately, the processed echo signals 17 are used to construct an image displayed on a graphic display 32. Input commands from an operator may be received via a keyboard 34 and/or a cursor control device 36 such as a mouse attached to the processor 33 as is well understood in the art.

In one embodiment, the ultrasonic imaging machine 11 may be an Aloka SSD 2000 scanner employing a phased array transducer with a center frequency of 3.5 MHz with a 6 dB band of 640 percent. Digitized echo signals from this ultrasonic imaging machine 11 may be captured by a Gage Applied Science 12100 A/D board and provided to the computer 30 for processing.

In one embodiment, the ultrasound imaging machine 11 may be a scanner that provides an interface that enables the user to utilize beam-steering on a linear array transducer. The ultrasound beam can be steered at different angles as shown in FIG. 1. The raw radio frequency data obtained at each beam-steered angle is stored on the ultrasound system for either off-line or real-time processing on the ultrasound system itself. The strain images or elastograms will be displayed alongside the ultrasound B-mode sonograms or superimposed on the ultrasound sonograms.

Figure 2:
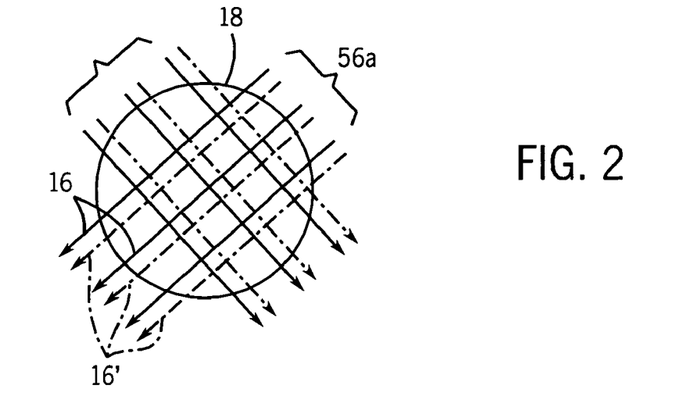
FIG. 2 is cross-sectional view of tissue showing collection of the ultrasonic echo signals obtained with the apparatus of FIG. 1 into echo signal sets having different ray angles.
Figure 9:
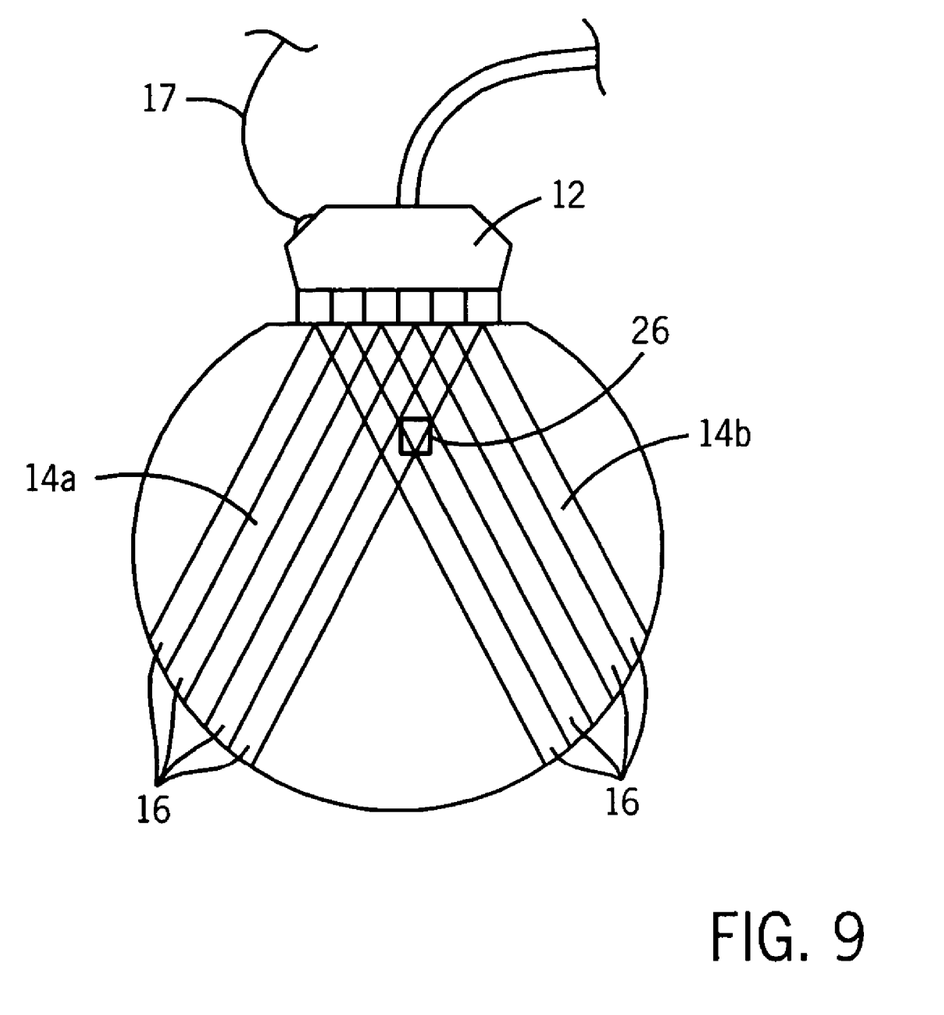
FIG. 9 is an ultrasonic transducer showing scanning using a multi-element phased-array linear or curvilinear transducer.

Generally, as shown in FIGS. 1 and 9, the ultrasound transducer 12 may be a single element transducer manually steered to acquire echo signals along different rays 16 of each ultrasonic beam 14, or be a multi-element ultrasonic transducer 12 electronically steered by phased array operation to acquire echo signals along different rays 16 of each ultrasonic beam 14. The ultrasonic transducer 12 may be manually repositioned for each of the different ultrasonic beams 14 or automatically moved by means of a motorized stage 42 receiving position signals 41 from the processor 33 via the interface circuitry 22. As shown in FIG. 2, a multi-element linear or curvilinear array ultrasonic transducer 12 may be steered to collect a series of angulated beams with minimal or no physical translation. Mechanical translation and angulation may also be used with multi-element phased array transducers.

A position sensor 19 may be attached to the ultrasonic transducer 12 to obtain position data 43 indicating the position and orientation of the ultrasonic transducer 12, or in the case where a motorized stage 42 is used, position data 43 may be extracted from the position signals 41 as the motorized stage 42 is moved.

Referring still to FIG. 1, during acquisition of the ultrasonic echo signals 17, compression is applied to the patient via a compression plate 44 oriented to compress the patient along a transmission axis 46 generally aligned with the center rays 16 of the ultrasonic beams 14. The compression plate 44 has a central aperture allowing the ultrasonic transducer 12 to transmit ultrasound therethrough. The compression plate 44 may be manually operated or may be operated by means of a compression signal 47 obtained from the interface circuitry 22 and received by actuators on the compression plate 44. Alternatively compression may be applied by the ultrasonic transducer 12 itself or other forms of compression may be used as are understood in the art. Alternatively, compression can be applied using the transducer itself, or with the attached compression plate in a freehand manner or using a motorized hand-held compressor for controlled compressions.

Figure 3:
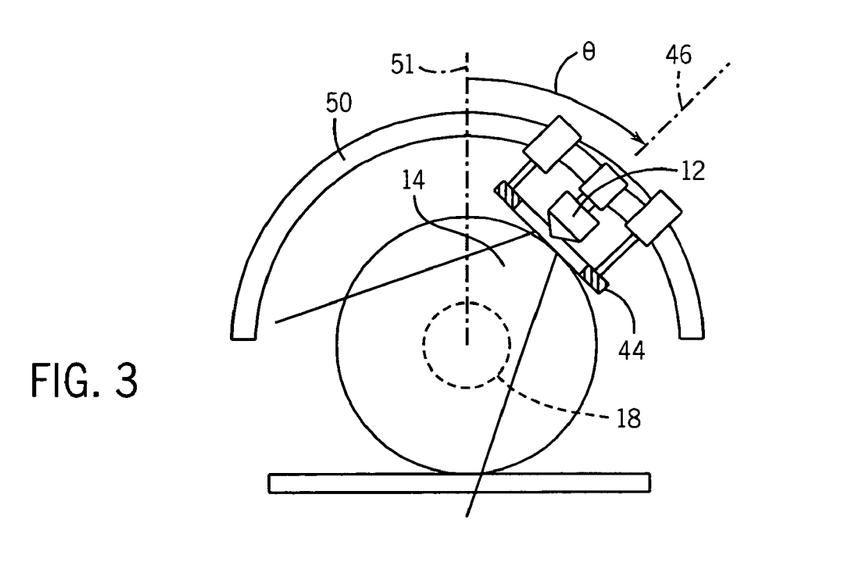
FIG. 3 is an alternative embodiment of the ultrasonic transducer system of FIG. 1 for multi-angled transducer and/or compression plate movement.

Referring now to FIG. 3 in an alternative embodiment of the invention, the motorized stage 42 of FIG. 1 may be replaced with an arcuate gantry arm 50 along which the ultrasonic transducer 12 may travel in an arc about the patient in region of interest 18, ideally over approximately 180 degrees. In this case ultrasonic beams 14 orbit about a center rather than translate as shown in FIG. 1. A compression plate 44 may be mounted with the ultrasonic transducer 12 to apply compressions along the transmission axis 46 or may be fixed at one angle independent from the transmission axis 46. Again, position signals 41 may control the position of the ultrasonic transducer 12 and compression signals may control the compression plate 44 and position data 43 provided to the processor 33.

Referring now to FIG. 2, echo signals 17 along rays 16, from either of the embodiments of FIG. 1 or 3, may be optionally collected in projection sets 56 (only two projection sets 56a and 56b are shown for clarity) such that echo signals 17 in each projection set 56 are along parallel rays 16. Each projection set will obtain two different echo signals 17 and 17'

(the latter indicated by dotted lines), one corresponding each to two different compression states of the compression plate 44.

The angle between measurement rays 16 of each projection set 56 may differ by as little as 0.75 degrees and still provide sufficient independence of measurement to reduce the statistical deviation in the measured strain. Nevertheless, higher degrees of angular separation may also be used and in a preferred embodiment, for example, forty-five different measurement sets 56 may be obtained, each with one degree difference between them. Clearly higher angular differences between the rays 16 or the measurement sets 56 produce even greater statistical independence in the measurements such as will help reduce noise. The invention contemplates that angular separations of five degrees or greater may also be practical over an angular ranges of up to 180 degrees. An optimal angular separation exists that will be used when possible under practical imaging conditions using beam-steering on a linear array transducer.

Figure 4:
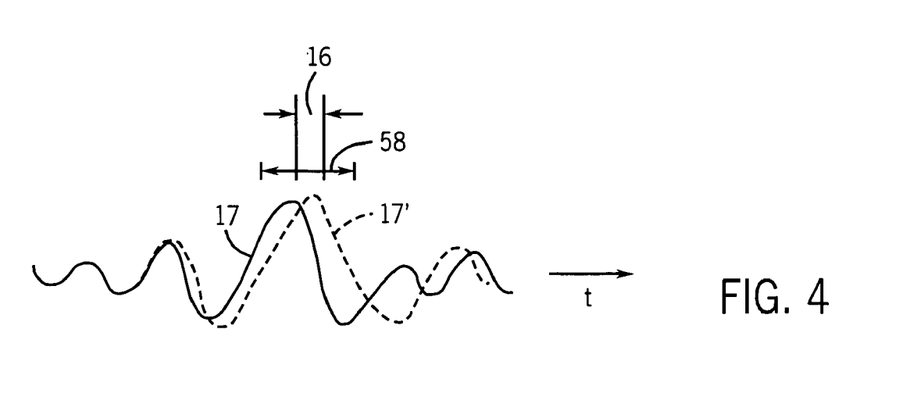
FIG. 4 is a simplified representation of two echo signals obtained in different compression states showing their relative displacement.

Referring now to FIG. 4, generally within each projection set 56, an echo signal 17 acquired during a first degree of compression (e.g., no compression) will differ from an echo signal 17' acquired during the second degree of compression (e.g., a predetermined positive compression) by a dilation of the echo signal 17' along the horizontal axis or time axis with respect to echo signal 17. In the example of FIG. 4, the echo signals 17 and 17' are raw ultrasound data, however, similar analysis can be performed with B-mode or amplitude envelope data.

As is understood in the art, for each pair of echo signals 17 and 17', relative displacement between the echo signals 17 and 17' at each point along the length of echo signals 17 and 17' are analyzed and through correlation or other techniques described generally in U.S. patent application Ser. No. 2003/30171672 A1, hereby incorporated by reference, to determine a displacement 60. This analysis is confined to a window 58 determined according to the desired resolution of strain measurement. This strain deduced from displacement 60 will be axial strain, that is strain measured along the transmission axis 46 of the echo signal 17. As is generally understood in the art, each window 58 may be identified with different volume elements 26 through which the particular rays 16 of echo signals 17 and 17' pass.

Figure 5:
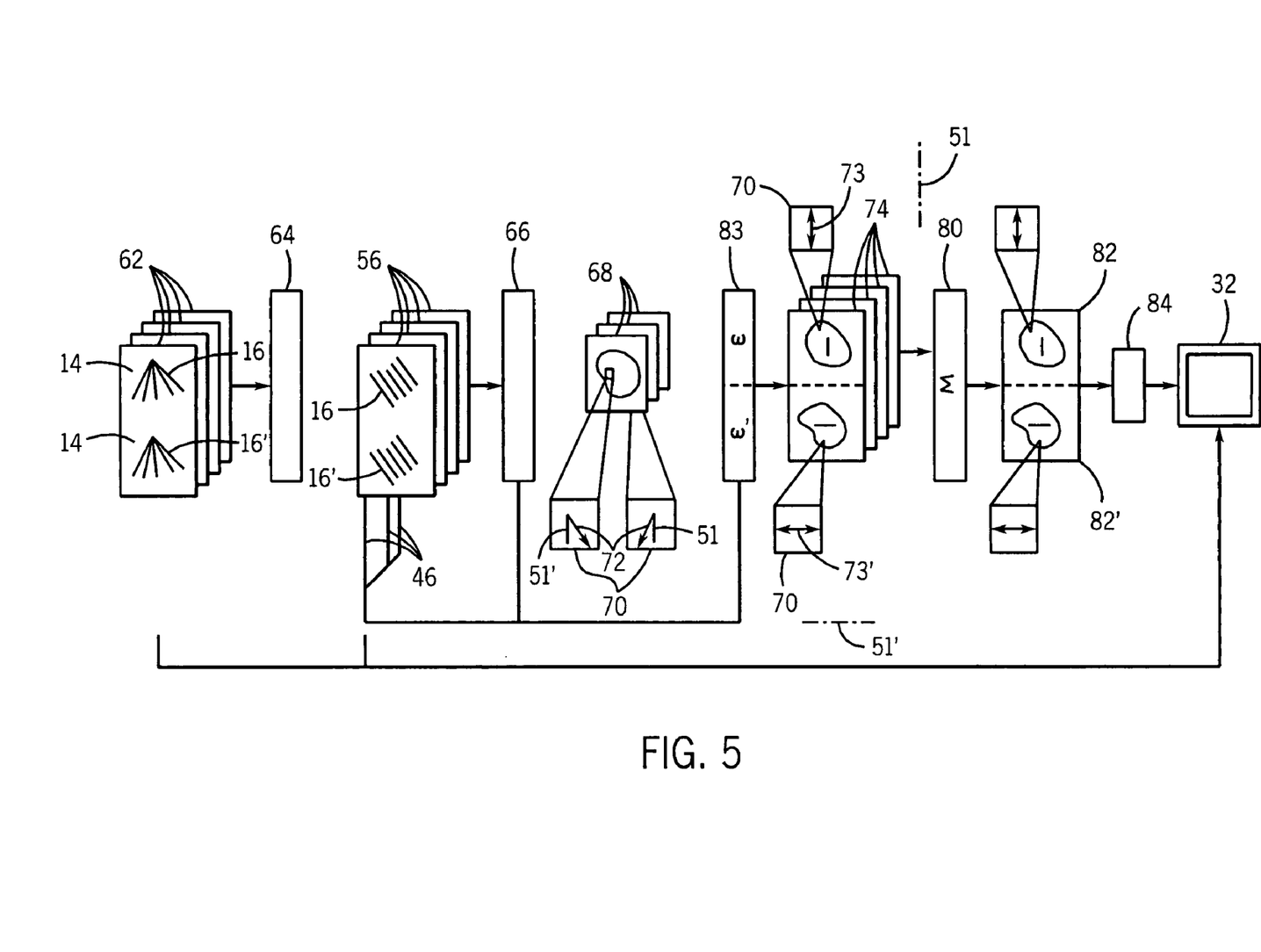
FIG. 5 is a signal flow diagram showing processing of the sets of FIG. 2 into angularly compounded elastographic images showing axial and lateral strain.

Referring now to FIG. 5 in a first step of the present invention, echo signal sets 62 are acquired, each including echo signals 17 and 17' at different compression amounts for one beam 14. Different echo signal sets 62 will hold data of different beams 14 taken at different locations and/or different angles by the apparatus described with respect to FIG. 1 or 4. The angle information of each echo signal 17 is preserved within the echo signal sets 62 as recorded by the processor 33 during acquisition of this data.

In a next step, the echo signal sets 62 are optionally provided to a rebinner 64 which separates them into parallel projection sets 56 described above, each again having echo signals 17 and 17' associated with two sets of compression, however, rebinned among echo signal sets 62 so that the echo signals of each projection set 56 are along parallel rays. The particular transmission axis 46 of the rays associated with each projection set 56 is determined and used later. Rebinning is necessary only when sector or phased array transducers are used.

A B-mode image (not shown) may be extracted from any or all of either the projection sets 56 or echo signal sets 62 to produce a reference image optionally to be projected together with the elastographic image on display 32.

The projection sets 56 may then be provided to a strain extracting block 66 which extracts strain information from the projection sets 56 by comparing the echo signals 17 and 17' as discussed above with respect to FIG. 4 to produce a series of elastographic images 68 corresponding generally to each of the projection sets 56. The elastographic images 68 will be composed of pixels 70, each representing a strain vector 72 having a magnitude proportional to the displacement 60 described above with respect to FIG. 4, and an angle determined from the transmission axis 46 described above.

The elastographic images 68 on a pixel by pixel basis are then weighted by weighting factors W and W' to extract weighted elastographic image pairs 74 comprised of an axial strain image 76 and a lateral strain image 76'. In this extraction, the pixels 70 of the axial image 76 provide strain extracted to a predetermined axial direction 51 and the pixel 70 of the image 76' provides extraction along a lateral direction 51' perpendicular to the axial direction 51. It will be understood that axial direction 51 and lateral direction 51' may be arbitrarily selected, however, typically the axial direction 51 will be along the direction of compression if there is one compression direction, and for the embodiment of FIG. 3 where the direction of compression is changing to a midrange of the gantry arm 50.

Figure 6:
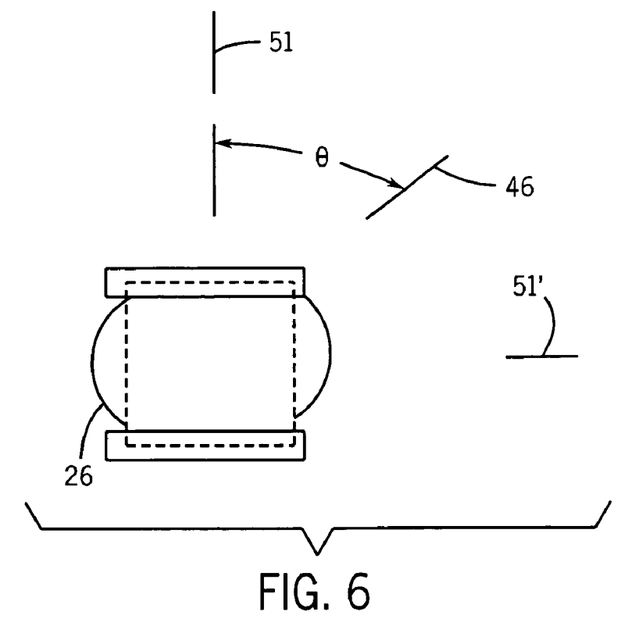
FIG. 6 is schematic representation of an individual voxel of tissue under compression showing angles used for the computation of the weighting factors of FIG. 5.

Referring now to FIG. 6, generally the weighting factor used for this extraction will be a function of the angle $\theta$ between the transmission axis 46 and the axial direction 51. The weighting factor may be derived using a variety of methods, however, in the preferred embodiment, it is deduced by assuming that the voxel 26 under compression along transmission axis 46 is an incompressible material, in other words, a material having a Poisson Ratio of approximately 0.5. In this case, a strain along transmission axis 46 may be multiplied by weight $w(\theta)$ to produce the equivalent expected strain along transmission axis 46 according to the following equation:

$$w(\theta) = \frac{1}{(\cos^2\theta - v\sin^2\theta)} \quad (1)$$

where $v$ is the Poisson's ratio is equal to 0.495 for incompressible media. Similarly, strain along transmission axis 46 may be multiplied by a slight variant of this weight W' to produce strain along lateral direction 51', per the following equation:

$$w(\theta) = \frac{1}{(\sin^2\theta - 1/v\cos^2\theta)} \quad (2)$$

Referring again to FIG. 5, the weighted strain vectors 72 of the pixels 70 in each of the images 68 are thus resolved to axial strain vectors 73 and lateral strain vectors 73' in elastographic image pairs 74 allowing like-oriented strain vectors of each of the elastographic image pairs 74 to be to be averaged per process block 80 to produce two images, an axial strain image 82 and a lateral strain image 82'. This summing process reduces the noise in each of the images 82 by an amount roughly equal to $\sqrt{N}$ where N is the number of images 68.

The axial strain image 82 and a lateral strain image 82' may be mapped by means of mapper 84 to the graphic display 32. For example, shades of gray may be used to map magnitudes of the axial strain and different colors may be used to map magnitudes of the lateral strain. Alternatively, the axial displacement and strain image 82 and lateral displacement and strain image 82' may be combined to produce shear strain images. Improved reconstruction of Young's Modulus images can also be obtained with more accurate normal and shear strain tensor information. A B-mode image may also be displayed next to or superimposed over the lateral image or switched with the lateral and axial images to provide a point of reference for the particular strain values.

Figure 7:
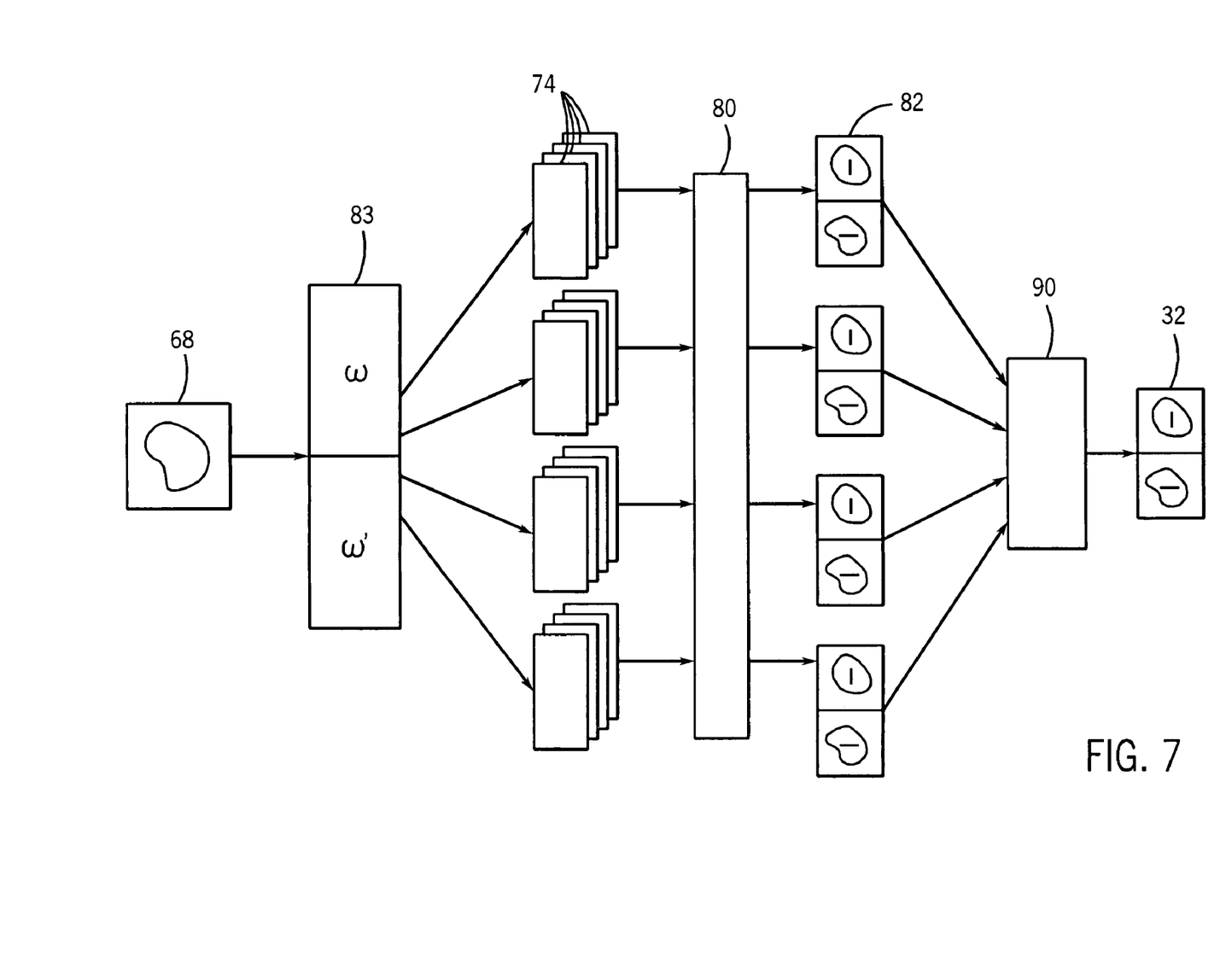
FIG. 7 is a flow diagram similar to that of FIG. 5 showing expansion of the technique to multiple compression angles.

Referring now to FIG. 7, the weighting block 83 may provide a more complex weighting system when the axis of compression may move. In this embodiment, weights from weighting block 83 are applied to the images 68 to produce a large number of compression identified elastographic image pairs 74 each associated with a different angle of compression axis. These may be combined per process block 80 as before to produce an axial strain image 82 and a lateral strain image 82' for each compression axis. Each of the axial strain image 82 and lateral strain image 82' may, in its own right, produce an image for a particular transmission axis 46 or they may be combined by a combiner 90 to produce some directionless quantity such as Poisson's Ratio or Young's Modulus from each of these different measurements, such as made to be displayed on graphic display 32.

Figure 8:
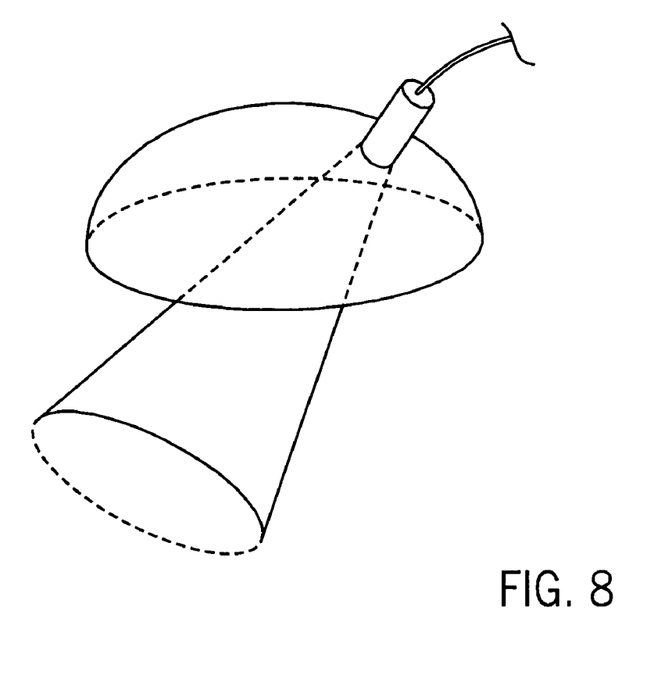
FIG. 8 is a perspective representation of the acquisition of scan data over a three-dimensional region of interest for parametric imaging of a volume rather than a single plane.

Referring now to FIG. 8 for reasons of clarity, the invention has been described with respect to voxels 26 aligned in a single plane corresponding to a plane of the image produced on graphic display 32. However, it will be understood the essential principle of summing together the echo signals taken at different angles to improve elastography measurements may occur by moving the ultrasonic transducer 12 so as to collect multiple ultrasonic beams that differ not only by their angle within the plane but also in angles over a three-dimensional curved surface so as to produce a volumetric image data that may be displayed one slice at a time or rendered as a three-dimensional object.

It will be understood generally that the order of combining the images and extracting the elastic strain information is arbitrary and that in certain instances the images may be combined first and then strain data extracted or strain data extracted and then combined in an angularly sensitive way.

It is specifically intended that the present invention not be limited to the embodiments and illustrations contained herein, but include modified forms of those embodiments including portions of the embodiments and combinations of elements of different embodiments as come within the scope of the following claims.

We claim:

1. An ultrasonic elastography system comprising:
an ultrasonic transducer system configured to provide a set of echo signals from at least two different angles over a plurality of voxels in a region of interest, the set of echo signals including first echo signals taken with tissue of the region of interest substantially at rest in a first compressive state and second echo signals taken with tissue of the region of interest substantially at rest in a second compressive state, each echo signal associated with a single different angle;
a memory device wherein the echo signals are stored for subsequent processing;
a processor executing a stored program to combine at least portions of echo signals from the different angles through a voxel, after they have been stored in the memory device, to produce at least one compounded strain measurement for the voxel in the region of interest along a predetermined single given angle, the compounded strain measurement being produced by determining relative displacement in time of the portions of the echo signals to deduce displacement between tissue between the first compressive state and the second compressive state; and
a graphic display communicating with the processor to receive and display the compounded strain measurement on the graphics display for viewing by a user of the ultrasonic elastography system.

2. The ultrasound elastography system of claim 1 wherein the processor receives the different angles of the ultrasonic echo signals underlying the compounded strain measurement to convert strain measurements derived from the ultrasonic echo signals underlying the compounded strain measurement to equivalent strain measurements along a predetermined strain axis of the single given angle; and combines the converted strain measurements to produce the compounded strain measurement.

3. The ultrasound elastography system of claim 2 wherein the predetermined strain axis is an axis of compression of the region of interest.

4. The ultrasound elastography system of claim 2 wherein the predetermined strain axis is perpendicular to an axis of compression of the region of interest.

5. The ultrasound elastography system of claim 2 wherein the conversion of strain measurements to equivalent strain measurement multiplies the strain measurements by a weighting function based on a difference between an angle of the strain measurement and the predetermined strain axis.

6. The ultrasound elastography system of claim 5 wherein the predetermined strain axis is an axis of compression of the region of interest and wherein the weighting function is $w(\theta) = 1/(\cos^2\theta - \nu \sin^2\theta)$;
where $\nu$ is an estimate of Poisson's ratio of the tissue of the region of interest; and
$\theta$ is the angle between the angle of the strain measurement and the predetermined strain axis.

7. The ultrasound elastography system of claim 5 wherein the predetermined strain axis is an axis perpendicular to an axis of compression of the region of interest and wherein the weighting function is $w(\theta) = 1/(\sin^2\theta - 1/\nu \cos^2\theta)$;
where $\nu$ is an estimate of Poisson's ratio of the tissue of the region of interest; and
$\theta$ is the angle between the angle of the strain measurement and the predetermined strain axis.

8. The ultrasound elastography system of claim 1 wherein the angle of compression changes with changes in the angle of the echo signal and wherein the predetermined strain axis is an axis angled with respect to the compression of the region of interest.

9. The ultrasound elastography system of claim 8 wherein the weighting function is $w(\theta) = 1/(\cos^2\theta - \nu \sin^2\theta)$;
where $\nu$ is an estimate of Poisson's ratio of the tissue of the region of interest; and
$\theta$ is the angle between the angle of the strain measurement and the predetermined strain axis.

10. The ultrasound elastography system of claim 1 wherein one compressive state is no compression.

11. The ultrasound elastography system of claim 1 wherein the processor combines the set of echo signals at the different angles to produce at least two compounded strain measurements of the voxel along at least two strain axes.

12. The ultrasound elastography system of claim 11 wherein the two strain axes are perpendicular.

13. The ultrasound elastography system of claim 11 wherein one of the two strain axes are perpendicular to the compression.

14. The ultrasound elastography system of claim 1 wherein the processor provides compounded strain measurements for multiple voxels to provide a strain image output.

15. The ultrasound elastography system of claim 1 wherein the processor provides an output of the group consisting of: Poisson's ratio of the tissue of the region of interest, and shear strain of the tissue of the region of interest.

16. The ultrasound elastography system of claim 1 wherein the processor receives a series of position signals from the ultrasonic transducer system and including a combiner using the position signals to match corresponding portions of the echo signals by voxel to produce the compounded strain measurement.

17. The ultrasound elastography system of claim 1 wherein the processor includes a correlator correlating values of the echo signals over each voxel to determine a maximum correlation and using the maximum correlation to match corresponding portions of the echo signals to produce the compounded strain measurement.

18. A method of ultrasonic elastography comprising the steps of:
(a) collecting with an ultrasonic transducer, at least two first echo signals from at least two different angles over a plurality of voxels in the region of interest in a first compressive state with tissue of the region of interest substantially at rest, each of the first echo signals associated with a single different angle;
(b) after step (a), collecting with the ultrasonic transducer at least two second echo signals from the different angles over the plurality of voxels in the region of interest in a second compressive state with tissue of the region of interest substantially at rest, each of the second echo signals associated with a single different angle;
(c) storing the collected signals of steps (a) and (b) in a memory device after collection of the signals at steps (a) and (b);
(d) after step (c), reading the collected signals from the memory device and combining at least portions of the first and the second echo signals from the different angles related to each voxel, to produce at least one compounded strain measurement for each voxel in the region of interest along a predetermined single given angle, the compounded strain measurement being produced from relative displacement in time of the portion of the echo signals related to each voxel to deduce displacement between tissue between the first compressive state and second compressive; and
(e) after step (d) displaying the compounded strain measurements for the voxels on a graphic display for viewing by a user.

19. The method of claim 18 wherein step (d) receives the different angles of the ultrasonic echo signals underlying the compounded strain measurement to convert strain measurements derived from the ultrasonic echo signals underlying the compounded strain measurement to equivalent strain measurements along a predetermined strain axis of the single given angle; and
combines the equivalent strain measurements to produce the compounded strain measurement.

20. The method of claim 19 wherein the predetermined strain axis is an axis of compression of the region of interest.

21. The method of claim 19 wherein the predetermined strain axis is perpendicular to an axis of compression of the region of interest.

22. The method of claim 19 wherein the conversion of strain measurements to equivalent strain measurement multiplies the strain measurements by a weighting function based on a difference between an angle of the strain measurement and the predetermined strain axis.

23. The method of claim 22 wherein the predetermined strain axis is an axis of compression of the region of interest and wherein the weighting function is $w(\theta)=1/(\cos^2\theta - \nu \sin^2\theta)$;
where $\nu$ is an estimate of Poisson's ratio of the tissue of the region of interest; and
$\theta$ is the angle between the angle of the strain measurement and the predetermined strain axis.

24. The method of claim 22 wherein the predetermined strain axis is an axis perpendicular to an axis of compression of the region of interest and wherein the weighting function is $w(\theta)=1/(\sin^2\theta - 1/\nu \cos^2\theta)$;
where $\nu$ is an estimate of Poisson's ratio of the tissue of the region of interest; and
$\theta$ is the angle between the angle of the strain measurement and the predetermined strain axis.

25. The method of claim 18 wherein the weighting function is $w(\theta)=1/(\cos^2\theta - \nu \sin^2\theta)$;
where $\nu$ is an estimate of Poisson's ration of the tissue of the region of interest; and
$\theta$ is the angle between the angle of the strain measurement and the predetermined strain axis.

26. The method of claim 18 wherein one compressive state is no compression.

27. The method of claim 18 wherein the processor combines the set of echo signals at the different angles to produce at least two compounded strain measurements of the voxel along at least two strain axes.

28. The method of claim 27 wherein the two strain axes are perpendicular.

29. The method of claim 27 wherein one of the two strain axes are perpendicular to the compression.

30. The method of claim 18 wherein step (d) produces compounded strain measurements for multiple voxels to provide a strain image output.

31. The method of claim 18 wherein step (d) provides an output of the group consisting of: Poisson's ratio of the tissue of the region of interest, and shear strain of the tissue of the region of interest.

32. The method of claim 18 including the step of receiving a series of position signals from the ultrasonic transducer and matching corresponding portions of the echo signals by voxel to produce the compounded strain measurement.

33. The method of claim 18 including the step of correlating values of the echo signals over each voxel to determine a maximum correlation, and using the maximum correlation to match corresponding portions of the echo signals, produce the compounded strain measurement.

34. The method of claim 18 wherein the echo signals are collected at angles differing by no more than 5 degrees.

35. The method of claim 18 wherein the echo signals are collected at angles differing by less than 1 degree.

36. The method of claim 18 wherein the echo signals are collected at angles ranging over 180 degrees.

37. The method of claim 18 wherein the echo signals are collected at angles ranging less than 90 degrees.

38. The method of claim 18 wherein the echo signals are collected of voxels aligned within a single image plane.

39. The method of claim 18 wherein the echo signals are collected of voxels distributed over a volume extending for multiple voxels in two dimensions perpendicular to a direction of ultrasonic propagation.

40. The ultrasound elastography system of claim 1 wherein the ultrasonic transducer system is a phased array transducer outputting the echo signals.

41. The method of claim 18 wherein step (a) employs a phased array transducer combining ultrasound signals to create the echo signals.

* * * * *

UNITED STATES PATENT AND TRADEMARK OFFICE
CERTIFICATE OF CORRECTION

PATENT NO.        : 7,601,122 B2                              Page 1 of 1
APPLICATION NO.   : 10/765293
DATED             : October 13, 2009
INVENTOR(S)       : James A. Zagzebski It is certified that error appears in the above-identified patent and that said Letters Patent is hereby corrected as shown below:

IN THE SPECIFICATION

Column 1, line 14, please amend the paragraph as follows:

-- This invention was made with ~~United States~~ government support under CA039224 awarded by the ~~following agencies: NIH CA 39224~~ National Institutes of Health. The ~~United States~~ government has certain rights in ~~this~~ the invention. --

Signed and Sealed this
Fourteenth Day of May, 2013

Teresa Stanek Rea
*Acting Director of the United States Patent and Trademark Office*